United States Patent
Samsoondar

(10) Patent No.: US 6,372,503 B1
(45) Date of Patent: Apr. 16, 2002

(54) CALIBRATOR MATERIAL FOR INSTRUMENTS WHICH MEASURE INTERFERENTS IN SERUM AND PLASMA SPECIMENS

(76) Inventor: James Samsoondar, 40 Hilborn Ave., Cambridge, Ontario (CA), N1G 1M7

( * ) Notice: Subject to any disclaimer, the term of this patent is extended or adjusted under 35 U.S.C. 154(b) by 0 days.

(21) Appl. No.: 09/147,373

(22) PCT Filed: Jun. 12, 1997

(86) PCT No.: PCT/CA97/00418

§ 371 Date: Dec. 11, 1998

§ 102(e) Date: Dec. 11, 1998

(87) PCT Pub. No.: WO97/47972

PCT Pub. Date: Dec. 18, 1997

(30) Foreign Application Priority Data

Jun. 12, 1996 (GB) .............................................. 9612264

(51) Int. Cl.$^7$ ................................................ G01N 31/00
(52) U.S. Cl. ............................ 436/8; 436/11; 436/12; 436/16; 436/66; 702/19
(58) Field of Search ................................ 436/8, 11, 12, 436/16, 19, 66, 69; 702/19

(56) References Cited

U.S. PATENT DOCUMENTS

| | | | | |
|---|---|---|---|---|
| 4,001,142 A | * | 1/1977 | Turner | ......................... 252/408 |
| 4,069,016 A | * | 1/1978 | Wu | |
| 4,116,336 A | * | 9/1978 | Sorensen et al. | ........ 206/524.8 |
| 4,297,143 A | * | 10/1981 | Kleinschmit | ................. 501/103 |
| 4,603,044 A | * | 7/1986 | Geho | ............................. 424/9 |
| 4,772,561 A | * | 9/1988 | Genshaw | ..................... 436/169 |
| 5,134,284 A | | 7/1992 | Volgyesi | |
| 5,278,073 A | * | 1/1994 | Grandjean | .................... 436/12 |
| 5,310,679 A | * | 5/1994 | Artiss et al. | ................... 436/18 |
| 5,447,838 A | * | 9/1995 | Meiklejohn | ..................... 435/5 |

FOREIGN PATENT DOCUMENTS

| | | |
|---|---|---|
| EP | 0 132 399 A | 1/1985 |
| EP | 0 210 417 A | 2/1987 |
| WO | WO 87/06343 | 10/1987 |
| WO | WO 87/06343 | * 10/1989 |

* cited by examiner

*Primary Examiner*—Maureen M. Wallenhorst
(74) *Attorney, Agent, or Firm*—Katten Muchin Zavis

(57) ABSTRACT

A quality control material is disclosed which is used to monitor the calibration or used for recalibration of instruments used to screen for interferents in serum or plasma specimens. In particular, the quality control material disclosed is used to monitor instrument calibrations or used for recalibration for instruments which assess the amount of hemolysis, turbidity, bilirubinemia and biliverdinemia, either separately, or any two, or any three, or all four simultaneously, in plasma or serum samples. The quality control material does not contain any blood products such as plasma lipids, bile pigments, or hemoglobin, is stable at room temperature, and is ready for use with up to four constituents.

79 Claims, 2 Drawing Sheets

CALIBRATOR MATERIAL FOR INSTRUMENTS WHICH MEASURE INTERFERENTS IN SERUM AND PLASMA SPECIMENS

TECHNICAL FIELD

This invention is in the field of spectrophotometric determinations of concentrations of substances in solution and relates to a quality control (QC) material for monitoring instrument precision on a daily basis In particular the QC material is used to monitor instruments which are used to screen for serum or plasma specimen quantities of various interferents, by measurement of the near infrared (NIR) radiation and the adjacent visible radiation transmitted through a sample in a labelled tube, a pipette tip, or any similar material through which radiation can pass. The material can also serve as calibrators.

BACKGROUND OF INVENTION

Clinical laboratory tests are routinely performed on the serum or plasma of whole blood. In a routine assay, red blood cells are separated from plasma by centrifugation, or red blood cells and various plasma proteins are separated from serum by clotting prior to centrifugation. Hemoglobin (Hb), light-scattering substances like lipid particles, and bile pigments bilirubin (BR) and biliverdin (BV) are typical substances which will interfere with and affect spectrophotometric and other blood analytical measurements. Such substances are referred to as interferents, and they can be measured spectrophotometrically. The presence of such interferents affects the ability to perform tests on the serum or plasma and as such can be said to compromise specimen integrity. An apparatus or instrument used for measuring interferents in serum and plasma i.e., assess specimen integrity, is a substitute for visual inspection. The interferents may be regarded as analytes, with respect to the instrument used to measure the interferents. Because quantitative results from the determination of the concentration of such interferents are reported based on specific calibration algorithms, there is a need to monitor calibration performance daily.

Internal quality control is a process used by all clinical laboratories for monitoring instrument calibration performance, particularly precision or reproducibility. It involves testing a stable material for the analyte(s) in question on a daily basis, and establishing target values for each analyte(s). Any stable material with similar spectral characteristics at selected wavelengths as the interferents under consideration, may be used as QC material, as long as a target value for the particular analyte can be assigned to it. Also, deviation from the target values resulting in violation of some pre-established rules, e.g., Westgard's multi-rules, should indicate a need for calibration adjustment or recalibration. Usually QC materials are tested daily, and at low, medium and high levels, in order to cover the dynamic range of a given assay. For any analyte, as long as the pre-established rules are not violated, the calibration algorithm for that analyte may be considered valid.

Accuracy or agreement with the true value or actual concentration of a particular analyte is usually not the primary concern with internal QC, therefore an accurate amount of the analyte does not have to be present in the QC material. However, concentrations of the interferents can be assigned to the QC material, and their predicted and assigned values can be used to adjust the initial calibration algorithms.

When recalibration is indicated, a series of 3 to 5 QC samples with assigned analyte concentrations (may be regarded as calibrators), can be used to make calibration adjustments; recalibration is not a simple process, and adjustment of the initial calibration for biases may be preferred.

DISCLOSURE OF INVENTION

The present invention provides a material which is able to allow for monitoring the calibration of spectrophotometric instruments which are used to measure concentrations of interferents using near infrared radiation and the adjacent visible radiation, and at the same time is stable at room temperature for a considerable period of time. The material can also be used to make calibration adjustments for biases, when necessary. This is also regarded as recalibration.

In its broad aspect the invention provides a quality control material for monitoring the calibration of instruments used to screen for interferents in serum or plasma specimens. In another aspect, the invention provides a quality control material to monitor the instrument calibrations for hemolysis, turbidity, bilirubinemia and biliverdinemia, either separately, or any two, or any three, or all four simultaneously, depending on the make-up of the quality control material. The material does not contain any blood products such as plasma lipids, bile pigments, or hemoglobin, is stable at room temperature, and is ready for use with up to four constituents.

In a further aspect, the invention provides a material and a method for monitoring the calibration of instruments used to screen for interferents in serum or plasma specimens using the quality control material of this invention.

In yet a further aspect, the invention provides a material and a method for adjusting the calibrations for biases, by using the slope and intercept of the linear regression equation obtained by plotting the assigned values of the respective interferents on the x-axis, and the predicted values, based on the original calibration algorithms, on the y-axis. This procedure is regarded herein as recalibration.

In a further aspect, the invention provides a substance with an absorbance spectrum which mimics the combined presence of hemoglobin, turbidity, bilirubin, and biliverdin at selected wavelengths in the 490 to 1085 nm region, and which combination of up to four substances provides a consistent stable composition.

In a particular embodiment, the invention relates to a composition containing amaranth, titanium dioxide, and methyl orange and biliverdin dihydrochloride. This composition is preferably prepared in a phosphate buffered saline and pH adjusted to about 7.4. In an alternative embodiment of this invention a lipid emulsion of any source commercially available, e.g., Intralipid™ (IL), can be used in place of titanium dioxide, methylene blue can be used in place of biliverdin dihydrochloride, and 10 millimoles per liter sodium bicarbonate must be used instead of the phosphate buffered saline. For stability, the latter can be sterilized by autoclaving. The amaranth is used to mimic hemoglobin, the titanium dioxide or IL is used to mimic turbidity, methyl orange is used to mimic bilirubin, and the methylene blue is used to mimic biliverdin. Other dyes may be used, for example, phenol red or basic fuchsin may be used to mimic hemoglobin; phenol red at acidic pH's or amaranth at slightly higher pH may be used to mimic bilirubin; azure, thionine, or toluidine blue O may be used in combination with amaranth, to mimic biliverdin. Also, in respect of alternatives to mimic turbidity, any substance which produces an absorbance pattern similar to the "apparent" absorbance in the region used by a calibration algorithm, may be used. One such example is copper sulfate. Turbidity causes an increase in the "apparent" absorbance. Apparent absorbance is based on the fact that transmitted light is measured and converted to absorbance units, therefore an instrument cannot distinguish true absorbance from loss of light due to scattering. In some cases, turbidity produces absorbance which is inversely proportional to wavelength. Turbidity is monitored by the slope of the absorbance curve at a single wavelength, namely, in the region greater than 800 nm.

In a preferred embodiment, the invention consists of amaranth, phenol red, copper sulfate, and toluidine blue O, in 100 millimoles per liter acetate buffer, pH 3 to 4. For low levels of BR, the amaranth can mimic both Hb and BR, making it possible to leave out phenol red. Within a given batch of QC material it is desirable to maintain a constant pH because spectral absorbance is affected by pH. Consequently, in a further aspect of the present invention, the pH of a given batch of QC material is maintained at a constant pH.

Figure 1:
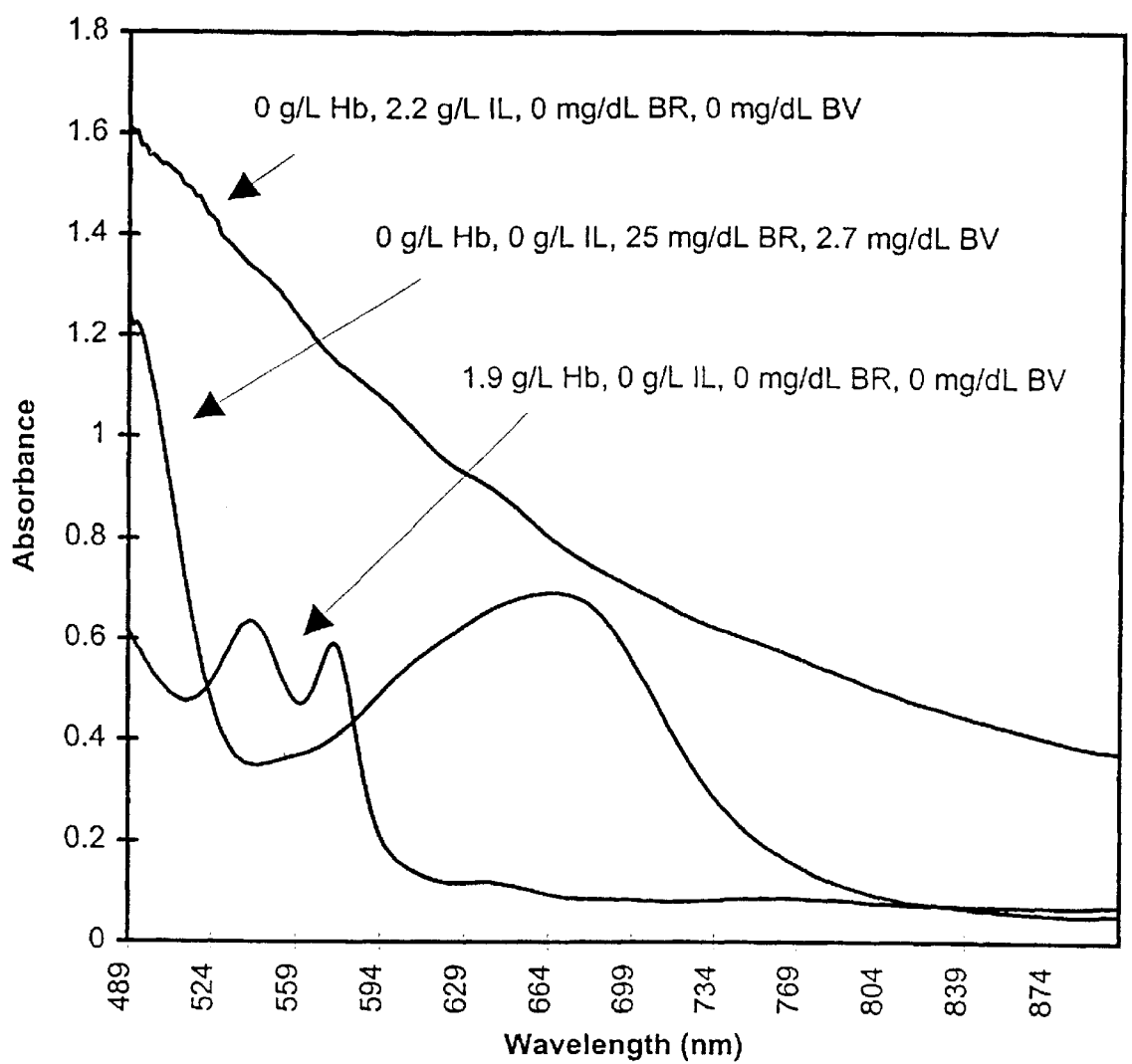
FIG. 1 is a graphic representation of the absorbance spectra of three different serum specimens, with added amount of interferents as shown.

As used herein, g/L means grams per liter and mg/dL means milligrams per deciliter.

DESCRIPTION OF PREFERRED EMBODIMENTS

Instruments designed to measure Hb as a measure of hemolysis, turbidity as an equivalent IL concentration, BR and BV, may require calibration adjustment or recalibration over a period of time. As a means of monitoring the calibration of such instruments for precision or reproducibility, a material of the present invention with the following composition, namely amaranth, phenol red, copper sulfate, and toluidine blue O, in 100 millimoles per liter acetate buffer, pH 3 to 4, can be used for monitoring such calibration. The concentrations of the substances will determine the assigned or target values of the analytes.

Furthermore, so long as the combination of these four substances provides a consistent stable composition, such material may be used. However, as will be understood by those practising in the art, any of such substances can be used alone or as a combination of two or three such substances, in any combination, depending upon the situation to be monitored, so long as the combination provides a consistent stable composition.

The QC material was made by combining different amounts of stock solutions of amaranth, phenol red, copper sulfate, and toluidine blue O, dissolved in 100 millimoles per liter acetate buffer with pH values between 3 and 4; the change in pH changes the assigned values of the analytes. The concentration of a stock solution will only serve as a guide to the amount of the stock which should be added to make a lot of QC material; the assigned or target value of an analyte will be determined by averaging the predicted concentrations of the interferents, using the appropriate calibration algorithm installed in the instrument used.

Where the material is sterilized by autoclave for long term storage, target values must be assigned to lots with the same concentrations of "interferents", after sterilization; the predicted levels include any changes due to the sterilization process. As an alternative for long term storage, sodium azide may be added; in respect of an embodiment the present invention with pH around 3 to 4, the acidic pH may be sufficient to prevent microbial growth.

Different calibration algorithms may be developed for any one type of tube, pipette tip, or similar translucent material, and also algorithms may be developed for several different types of tubes combined or different translucent materials combined. The calibration algorithms installed in the instrument used to test the QC material of the present disclosure were developed for measurement in translucent pipette tips. These algorithms are as follows:

Hemolysis Algorithm $$(g/L)\ Hb = 30.14\ (591\ nm) - 27.98\ (610\ nm)$$

where (Wnm) is the first derivative of the absorbance measurement at the wavelength specified.

Turbidity Algorithm $$g/L\ IL = 296.01\ (900\ nm) - 0.04$$

where (Xnm) is the raw absorbance measurement at the wavelength specified.

Bilirubin Algorithm $$mg/dL\ BR = 142.09\ (511\ nm) + 89.9\ (554\ nm) - 4.47$$

where (Ynm) is the first derivative of the absorbance measurement at the wavelength specified.

Biliverdin Algorithm $$mg/dL\ BV = 160.29\ (718\ nm) - 206.15\ (781\ nm) + 1.42$$

where (Znm) is the first derivative of the absorbance measurement at the wavelength specified.

Figure 2:
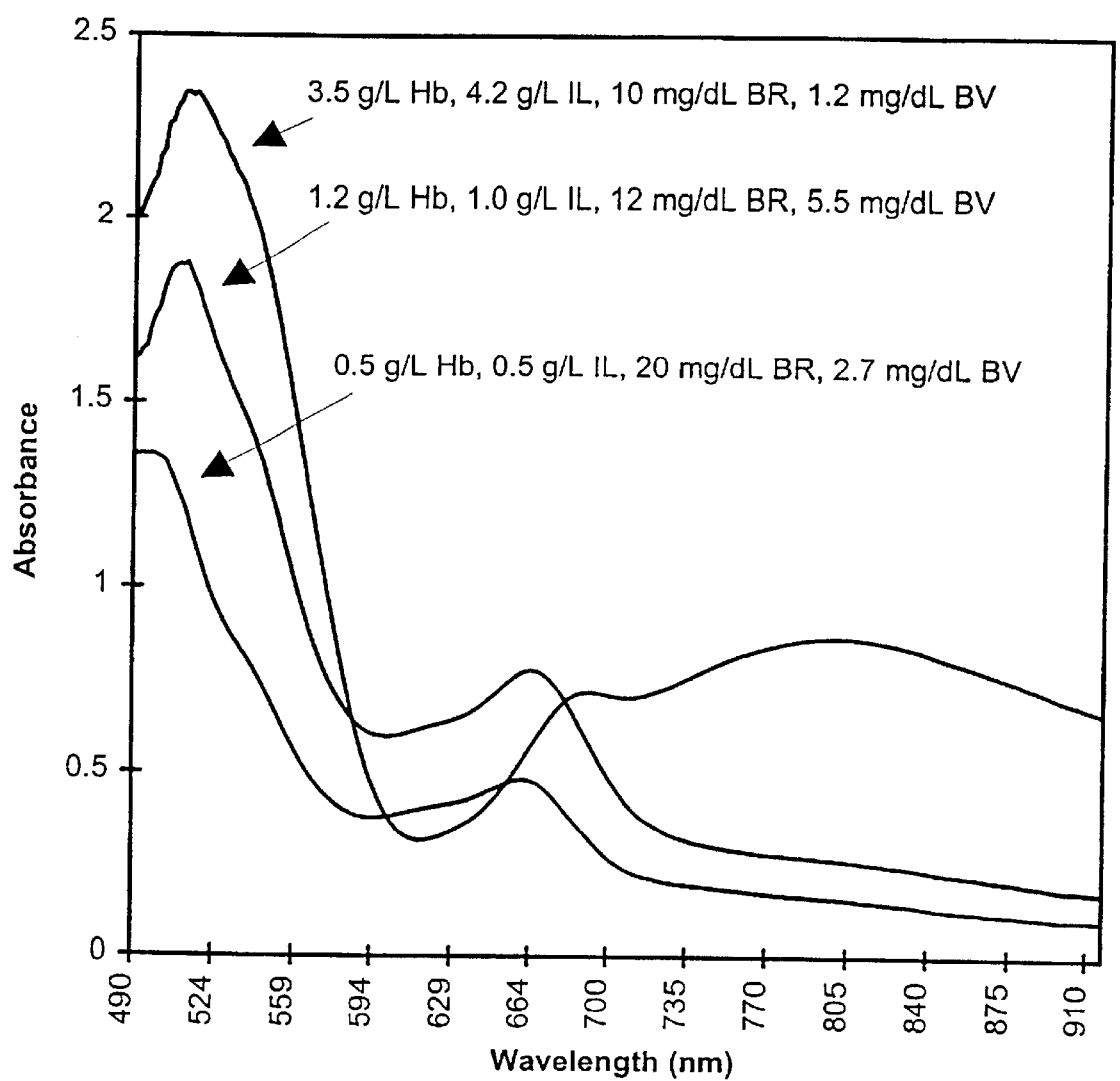
FIG. 2 is a graphic representation of the absorbance spectra of three different mixtures of the quality control material, with predicted interferent concentrations as shown.

The calibration algorithms listed above are just examples, used to relate the spectra with their associated levels of the four analytes or interferents. The algorithms along with the absorbance measurements of respective samples are used to predict the levels of the four analytes. Sample spectra of three different serum specimens spiked with interferents, are shown in FIG. 1, and sample spectra of three different mixtures of the QC material are shown in FIG. 2. The predicted concentrations of the interferents in the QC samples are shown in FIG. 2.

With respect to FIGS. 1 and 2, the serum specimens possessed varying degrees of hemolysis, turbidity, and bile pigmentation, and the QC specimens mimicked serum or plasma specimens with different levels of interferents. Although the present description has been concerned with a QC material containing four substances, it is to be understood that the QC material can be used to monitor calibration for any one, two, three, or all four interferents simultaneously.

While the invention has been particularly shown and described with reference to preferred embodiments, it will be understood by those skilled in the art that various other changes in form and detail may be made without departing from the spirit and scope of the invention.

I claim:

1. A quality control material comprising two or more substances which mimic two or more of an indicator of hemolysis, turbidity, bilirubin, and biliverdin.

2. The quality control material of claim 1 wherein pH is maintained at a constant value.

3. The quality control material of claim 1 wherein the indicator of hemolysis is hemoglobin.

4. The quality control material of claim 3 wherein said substance used to mimic hemoglobin is selected from the group consisting of amaranth, phenol red and basic fuchsin.

5. The quality control material of claim 1 wherein said substance used to mimic turbidity is selected from the group consisting of titanium dioxide, copper sulfate and lipid emulsion.

6. The quality control material of claim 1 wherein said substance used to mimic bilirubin is selected from the group consisting of methyl orange, amaranth, and phenol red.

7. The quality control material of claim 1 wherein said substance used to mimic biliverdin is selected from the group consisting of methylene blue, azure, thionine and toluidine blue O.

8. The quality control material of claim 1 wherein said substance used to mimic an indicator of hemolysis is a substance that mimics hemoglobin and is selected from the group consisting of amaranth, phenol red and basic fuchsin; said substance used to mimic turbidity is selected from the group consisting of titanium dioxide, copper sulfate and lipid emulsion; said substance used to mimic bilirubin is selected from the group consisting of methyl orange, amaranth, and phenol red; and said substance used to mimic biliverdin is selected from the group consisting of methylene blue, azure, thionine and toluidine blue O.

9. The quality control material of claim 8 wherein pH is maintained at a constant value.

10. A quality control material comprising one or more substances each of which mimics an indicator of hemolysis and one or more substances, which mimic one or more of turbidity, bilirubin, and biliverdin.

11. The quality control material of claim 10 wherein said indicator of hemolysis is hemoglobin.

12. The quality control material of claim 11 wherein said substance used to mimic hemoglobin is selected from the group consisting of amaranth, phenol red and basic fuchsin.

13. The quality control material of claim 10 wherein said substance used to mimic turbidity is selected from the group consisting of titanium dioxide, copper sulfate and lipid emulsion.

14. The quality control material of claim 10 wherein said substance used to mimic bilirubin is selected from the group consisting of methyl orange, amaranth, and phenol red.

15. The quality control material of claim 10 wherein said substance used to mimic biliverdin is selected from the group consisting of methylene blue, azure, thionine and toluidine blue O.

16. The quality control material of claim 10 wherein said substance used to mimic an indicator of hemolysis is selected from the group consisting of amaranth, phenol red and basic fuchsin; said substance used to mimic turbidity is selected from the group consisting of titanium dioxide, copper sulfate and lipid emulsion; said substance used to mimic bilirubin is selected from the group consisting of methyl orange, amaranth, and phenol red; and said substance used to mimic biliverdin is selected from the group consisting of methylene blue, azure, thionine and toluidine blue O.

17. The quality control material of claim 16 wherein pH is maintained at a constant value.

18. A quality control material, for use in an instrument designed to measure biliverdin and optionally one or more of hemoglobin, turbidity, or bilirubin, said material comprising one or more separate substances, one of which mimics biliverdin and optionally one or more of which mimic hemoglobin, turbidity, and bilirubin, respectively wherein the substance used to mimic biliverdin is selected from the group consisting of methylene blue, azure, thionine and toluidine blue O.

19. A method of monitoring calibration of an instrument comprising a calibration algorithm for biliverdin and optionally one or more calibration algorithms for hemolysis, turbidity, or bilirubin, said method comprising:

i) measuring absorbance of said quality control material of claim 18 with said instrument to obtain one or more measurements;

ii) calculating one or more concentration values from said one or more measurements;

iii) comparing said one or more concentration values with one or more assigned values given to said quality control material; and iv) determining if there is a violation of a pre-established quality control rule, thereby monitoring said calibration algorithms of said instrument.

20. A method of recalibrating an instrument comprising a calibration algorithm for biliverdin and optionally one or more calibration algorithms for hemolysis, turbidity, or bilirubin, said method comprising:

i) measuring absorbance of at least two of said quality control materials of claim 18 with said instrument to obtain a measurement for each of said quality control materials;

ii) calculating a concentration value from each of said measurements to provide calculated concentrations;

iii) establishing a slope and intercept by linear regression using each of said calculated concentrations of said quality control materials; and iv) adjusting calculated concentration values of samples using said slope and intercept, thereby recalibrating the instrument.

21. A quality control material, for use in an instrument designed to measure biliverdin and optionally one or more of hemoglobin, turbidity, or bilirubin, said material comprising one or more separate substances, one of which mimics biliverdin and optionally one of each of which mimics hemoglobin, turbidity, and bilirubin, respectively, wherein the substance used to mimic hemoglobin is selected from the group consisting of amaranth, phenol red and basic fuchsin; said substance used to mimic turbidity is selected from the group consisting of titanium dioxide, copper sulfate and lipid emulsion; said substance used to mimic bilirubin is selected from the group consisting of methyl orange, amaranth, and phenol red; and said substance used to mimic biliverdin is selected from the group consisting of methylene blue, azure, thionine and toluidine blue O.

22. A method of monitoring calibration of an instrument comprising a calibration algorithm for biliverdin and optionally one or more calibration algorithms for hemolysis, turbidity, or bilirubin, said method comprising:

i) measuring absorbance of said quality control material of claim 21 with said instrument to obtain one or more measurements;

ii) calculating one or more concentration values from said one or more measurements;

iii) comparing said one or more concentration values with one or more assigned values given to said quality control material; and iv) determining if there is a violation of a pre-established quality control rule, thereby monitoring said calibration algorithms of said instrument.

23. A method of recalibrating an instrument comprising a calibration algorithm for biliverdin and optionally one or more calibration algorithms for hemolysis, turbidity, or bilirubin, said method comprising:

i) measuring absorbance of at least two of said quality control materials of claim 21 with said instrument to obtain a measurement for each of said quality control materials;

ii) calculating a concentration value from each of said measurements to provide calculated concentrations;

iii) establishing a slope and intercept by linear regression using each of said calculated concentrations of said quality control materials; and iv) adjusting calculated concentration values of samples using said slope and intercept, thereby recalibrating the instrument.

24. A quality control material, for use in an instrument designed to measure one or more of hemoglobin, turbidity, bilirubin, or biliverdin, wherein said instrument requires calibration or recalibration, said material comprising amaranth, phenol red, copper sulfate, and toluidine blue O in 100 millimoles per liter acetate buffer, and the pH of said material is 3 to 4.

25. A quality control material, comprising a substance which mimics an indicator of hemolysis wherein said indicator of hemolysis consists of s single substance, where said substance is amaranth, and said amaranth is used to mimic both an indicator of hemolysis and bilirubin where the concentration of bilirubin is less than 10 mg/dL.

26. A quality control material comprising amaranth, lipid emulsion, and one of methylene blue, azure, thionine, or toluidine blue O.

27. A method of monitoring calibration of an instrument comprising a calibration algorithm for an indicator of hemolysis in serum or plasma, said method comprising:

i) measuring absorbance of a quality control material with said instrument to obtain a measurement, said quality control material comprising one or more substances that mimics an indicator of hemolysis;

ii) calculating a concentration value from said measurement;

iii) comparing said concentration value with an assigned value given to said quality control material; and iv) determining if there is a violation of a pre-established quality control rule, thereby monitoring said calibration algorithm of said instrument.

28. The method of claim 27 wherein pH of said quality control material is maintained at a constant value.

29. The method of claim 27 wherein the indicator of hemolysis is hemoglobin.

30. The method of claim 27 wherein said substance used to mimic hemolysis is selected from the group consisting of amaranth, phenol red and basic fuchsin.

31. The method of claim 30 wherein said substance is amaranth.

32. The method of claim 31 wherein the pH of said quality control material is maintained at a constant value.

33. A method of recalibrating an instrument comprising a calibration algorithm for hemolysis, said method comprising:

i) measuring absorbance of at least two quality control materials with said instrument to obtain a measurement for each of said quality control materials, said quality control materials comprising a substance that mimics hemoglobin, and wherein said substance used to mimic hemoglobin is selected from the group consisting of amaranth, phenol red and basic fuchsin;

ii) calculating a concentration value from each of said measurements to provide calculated concentrations;

iii) establishing a slope and intercept by linear regression using each of said calculated concentrations; and iv) adjusting calculated concentration values of samples using said slope and intercept, thereby recalibrating said instrument.

34. The method of claim 33 wherein said substance is amaranth.

35. The method of claim 34 wherein the pH of said quality control materials is maintained at a constant value.

36. A method of monitoring calibration of an instrument comprising two or more calibration algorithms for two or more of hemolysis, turbidity, bilirubin or biliverdin said method comprising:

i) measuring absorbance of a quality control material with said instrument to obtain one or more measurements, said quality control material comprising one or more substances which mimics two or more of an indicator of hemolysis, turbidity, bilirubin, and biliverdin;

ii) calculating one or more concentration values from said one or more measurements;

iii) comparing said one or more concentration values with one or more assigned values given to said quality control material; and iv) determining if there is a violation of a pre-established quality control rule, thereby monitoring said calibration algorithms of said instrument.

37. The method of claim 36 wherein the pH of said quality control material is maintained at a constant value.

38. The method of claim 36 wherein in said step of measuring, said indicator of hemolysis is hemoglobin.

39. The method of claim 38 wherein said substance used to mimic hemoglobin is selected from the group consisting of amaranth, phenol red and basic fuchsin.

40. The method of claim 36 wherein in said step of measuring, said substance used to mimic turbidity is selected from the group consisting of titanium dioxide, copper sulfate and lipid emulsion.

41. The method of claim 36 wherein in said step of measuring, said substance used to mimic bilirubin is selected from the group consisting of methyl orange, amaranth, and phenol red.

42. The method of claim 36 wherein said substance used to mimic biliverdin is selected from the group consisting of methylene blue, azure, thionine and toluidine blue O.

43. The method of claim 36 wherein in said step of measuring, said substance used to mimic an indicator of hemolysis is selected from the group consisting of amaranth, phenol red and basic fuchsin; said substance used to mimic turbidity is selected from the group consisting of titanium dioxide, copper sulfate and lipid emulsion; said substance used to mimic bilirubin is selected from the group consisting of methyl orange, amaranth, and phenol red; and said substance used to mimic biliverdin is selected from the group consisting of methylene blue, azure, thionine and toluidine blue O.

44. The method of claim 43 wherein the pH of said quality control material is maintained at a constant value.

45. A method of recalibrating an instrument comprising two or more calibration algorithms for two or more of hemolysis, turbidity, bilirubin or biliverdin said method comprising:

i) measuring absorbance of at least two quality control materials with said instrument, to obtain a measurement for each of said quality control materials, said quality control materials comprising one or more substances which mimic two or more of an indicator of hemolysis, turbidity, bilirubin, and biliverdin, respectively;

ii) calculating a concentration value from each of said measurements to provide calculated concentrations;

iii) establishing a slope and intercept by linear regression using each of said calculated concentrations of said quality control materials; and iv) adjusting calculated concentration values of samples using said slope and intercept, thereby recalibrating said instrument.

46. The method of claim 45 wherein, in said step of measuring, the pH of said quality control materials is maintained at a constant value.

47. The method of claim 45 wherein, in said step of measuring, said indicator of hemolysis is hemoglobin.

48. The method of claim 47 wherein said substance used to mimic hemoglobin is selected from the group consisting of amaranth, phenol red and basic fuchsin.

49. The method of claim 45 wherein, in said step of measuring, said substance used to mimic turbidity is selected from the group consisting of titanium dioxide, copper sulfate and lipid emulsion.

50. The method of claim 45 wherein, in said step of measuring, said substance used to mimic bilirubin is selected from the group consisting of methyl orange, amaranth, and phenol red.

51. The method of claim 45 wherein, in said step of measuring, said substance used to mimic biliverdin is selected from the group consisting of methylene blue, azure, thionine and toluiding blue O.

52. The method of claim 45 wherein, in said step of measuring, said substance used to mimic an indicator of hemolysis is selected from the group consisting of amaranth, phenol red and basic fuchsin; said substance used to mimic turbidity is selected from the group consisting of titanium dioxide, copper sulfate and lipid emulsion; said substance used to mimic bilirubin is selected from the group consisting of methyl orange, amaranth, and phenol red; and said substance used to mimic biliverdin is selected from the group consisting of methylene blue, azure, thionine and toluidine blue O.

53. The method of claim 52 wherein the pH of said quality control material is maintained at a constant value.

54. A method of monitoring calibration of an instrument comprising a calibration algorithm for hemolysis and one or more calibration algorithms for turbidity, bilirubin or biliverdin said method comprising:

i) measuring absorbance of a quality control material with said instrument, to obtain one or more measurements, said quality control material comprising one or more substances which mimic an indicator of hemolysis and one or more substances which mimic one or more of turbidity, bilirubin, and biliverdin, respectively;

ii) calculating one or more concentration values from said one or more measurements;

iii) comparing said one or more concentration values with one or more assigned values given to said quality control material; and iv) determining if there is a violation of a pre-established quality control rule, thereby monitoring said calibration algorithms of said instrument.

55. The method of claim 54 wherein the pH of said quality control material is maintained at a constant value.

56. The method of claim 54 wherein, in said step of measuring, said indicator of hemolysis is hemoglobin.

57. The method of claim 56 wherein said substance used to mimic hemoglobin is selected from the group consisting of amaranth, phenol red and basic fuchsin.

58. The method of claim 54 wherein, in said step of measuring, said substance used to mimic turbidity is selected from the group consisting of titanium dioxide, copper sulfate and lipid emulsion.

59. The method of claim 54 wherein, in said step of measuring, said substance used to mimic bilirubin is selected from the group consisting of methyl orange, amaranth, and phenol red.

60. The method of claim 54 wherein, in said step of measuring, said substance used to mimic biliverdin is selected from the group consisting of methylene blue, azure, thionine and toluiding blue O.

61. The method of claim 54 wherein, in said step of measuring, said substance used to mimic an indicator of hemolysis is selected from the group consisting of amaranth, phenol red and basic fuchsin; said substance used to mimic turbidity is selected from the group consisting of titanium dioxide, copper sulfate and lipid emulsion; said substance used to mimic bilirubin is selected from the group consisting of methyl orange, amaranth, and phenol red; and said substance used to mimic biliverdin is selected from the group consisting of methylene blue, azure, thionine and toluidine blue O.

62. The method of claim 61 wherein the pH of said quality control material is maintained at a constant value.

63. A method of recalibrating an instrument comprising a calibration algorithm for hemolysis and one or more calibration algorithms for turbidity, bilirubin or biliverdin, said method comprising:

i) measuring absorbance of at least two quality control materials with said instrument, to obtain a measurement for each of said quality control materials, said quality control materials consisting of a substance which mimics an indicator of hemolysis and one or more substances which mimic turbidity, bilirubin, and biliverdin,;

ii) calculating a concentration value from each of said measurements to provide calculated concentrations;

iii) establishing a slope and intercept by linear regression using each of said calculated concentrations; and iv) adjusting calculated concentration values of samples using said slope and intercept, thereby recalibrating the instrument.

64. The method of claim 63 wherein the pH of said quality control materials is maintained at a constant value.

65. The method of claim 63 wherein, in said step of measuring, said indicator of hemolysis is hemoglobin.

66. The method of claim 65 wherein said substance which mimics an indicator of hemolysis is selected from the group consisting of amaranth, phenol red, and basic fuschin.

67. The method of claim 63 wherein, in said step of measuring, said substance used to mimic turbidity is selected from the group consisting of titanium dioxide, copper sulfate and lipid emulsion.

68. The method of claim 63 wherein, in said step of measuring, said substance used to mimic bilirubin is selected from the group consisting of methyl orange, amaranth, and phenol red.

69. The method of claim 63 wherein, in said step of measuring, said substance used to mimic biliverdin is selected from the group consisting of methylene blue, azure, thionine and toluidine blue O.

70. A method of claim 63 wherein, in said step of measuring, said substance used to mimic an indicator of hemolysis is selected from the group consisting of amaranth, phenol red and basic fuchsin; said substance used to mimic turbidity is selected from the group consisting of titanium dioxide, copper sulfate and lipid emulsion; said substance used to mimic bilirubin is selected from the group consisting of methyl orange, amaranth, and phenol red; and said substance used to mimic biliverdin is selected from the group consisting of methylene blue, azure, thionine and toluidine blue O.

71. The method of claim 70 wherein the pH of said quality control materials is maintained at a constant value.

72. A method for monitoring the calibration of an instrument comprising one or more calibration algorithms for hemolysis, turbidity, bilirubin or biliverdin said method comprising:
  i) measuring absorbance of a quality control material with said instrument to obtain one or more measurements, said quality control material comprising amaranth, phenol red, copper sulfate, and toluidine blue O in 100 millimoles per liter acetate buffer, and pH of said quality control material is 3 to 4;
  ii) calculating one or more concentration values from said one or more measurements;
  iii) comparing said one or more concentration values with one or more assigned values given to said quality control material; and
  iv) determining if there is a violation of a pre-established quality control rule, thereby monitoring said calibration algorithms of said instrument.

73. The method of claim 72 where, in said step of measuring, amaranth is used to mimic both an indicator of hemolysis, wherein the indicator of hemolysis is hemoglobin, and bilirubin, where the concentration of bilirubin is less than 10 mg/dL.

74. A method for monitoring the calibration of an instrument comprising one or more calibration algorithms for hemolysis, turbidity, bilirubin or biliverdin said method comprising:
  i) measuring absorbance of a quality control material with said instrument to obtain one or more measurements, said quality control material comprising amaranth, lipid emulsion, and one of methylene blue, azure, thionine or toluidine blue O;
  ii) calculating one or more concentration values from said one or more measurements;
  iii) comparing said one or more concentration values with one or more assigned values given to said quality control material; and
  iv) determining if there is a violation of a pre-established quality control rule, thereby monitoring said calibration algorithms of said instrument.

75. A method of recalibrating an instrument comprising one or more calibration algorithms for hemolysis, turbidity, bilirubin or biliverdin said method comprising:
  i) measuring absorbance of at least two quality control materials with said instrument to obtain a measurement for each of said quality control materials, said quality control materials comprising amaranth, phenol red, copper sulfate, and toluidine blue O in 100 millimoles per liter acetate buffer, and pH of said quality control materials is 3 to 4;
  ii) calculating a concentration value from each of said measurements to provide calculated concentrations;
  iii) establishing a slope and intercept by linear regression using each of said calculated concentrations of said quality control materials; and
  iv) adjusting calculated concentration values of samples using said slope and intercept, thereby recalibrating the instrument.

76. The method of claim 75 wherein, in said step of measuring, amaranth is used to mimic both an indicator of hemolysis, wherein the indicator of hemolysis is hemoglobin, and bilirubin, where the concentration of bilirubin is less than 10 mg/dL.

77. A method of recalibrating an instrument comprising one or more calibration algorithms for hemolysis, turbidity, bilirubin or biliverdin said method comprising:
  i) measuring absorbance of at least two quality control materials with said instrument to obtain a measurement for each of said quality control materials, said quality control materials comprising amaranth, lipid emulsion, and one of methylene blue, azure, thionine or toluidine blue O;
  ii) calculating a concentration value from each of said measurements to provide calculated concentrations;
  iii) establishing a slope and intercept by linear regression using each of said calculated concentrations of said quality control materials; and
  iv) adjusting calculated concentration values of samples using said slope and intercept, thereby recalibrating the instrument.

78. A method of monitoring the calibration of an instrument comprising a calibration algorithm for biliverdin and one or more calibration algorithms for hemolysis, turbidity or bilirubin, said method comprising:
  i) measuring absorbance of a quality control material with said instrument to obtain one or more measurements, said quality control material comprising one or more substances, one of which mimics biliverdin and at least one of which mimics hemoglobin, turbidity, and bilirubin, wherein said substance used to mimic biliverdin is selected from the group consisting of methylene blue, Azure, thionine, and toluidine blue O;
  ii) calculating one or more concentration values from said one or more measurements;
  iii) comparing said one or more concentration values with one or more assigned values given to said quality control material; and
  iv) determining if there is a violation of a pre-established quality control rule, thereby monitoring said calibration algorithms of said instrument.

79. A method of monitoring the calibration of an instrument comprising one or more calibration algorithms for an indicator of hemolysis, turbidity, bilirubin or biliverdin in serum or plasma, said method comprising:
  i) measuring absorbance of a quality control material with said instrument to obtain one or more measurements, said quality control material comprising one or more substances which mimic one or more of an indicator of hemolysis, turbidity, bilirubin, and biliverdin;
  ii) calculating one or more concentration values from said one or more measurements;
  iii) comparing said one or more concentration values with one or more assigned values given to said quality control material; and
  iv) determining if there is a violation of a pre-established quality control rule, thereby monitoring said one or more calibration algorithms of said instrument.

* * * * *